US010968422B2

(12) United States Patent
Casset et al.

(10) Patent No.: US 10,968,422 B2
(45) Date of Patent: Apr. 6, 2021

(54) DEVICE FOR TREATING AT LEAST ONE BIOLOGICAL CELL, NOTABLY WITH A VIEW TO INTRACELLULAR DELIVERY

(71) Applicants: Commissariat A L'Energie Atomique et aux Energies Alternatives, Paris (FR); INSTITUT NATIONAL DE LA SANTE ET DE LA RECHERCHE MEDICALE (INSERM), Paris (FR)

(72) Inventors: Fabrice Casset, Tencin (FR); Arnaud Millet, Voreppe (FR)

(73) Assignees: Commissariat A L'Energie Atomique et aux Energies Alternatives, Paris (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 44 days.

(21) Appl. No.: 15/335,702

(22) Filed: Oct. 27, 2016

(65) Prior Publication Data

US 2017/0121661 A1    May 4, 2017

(30) Foreign Application Priority Data

Oct. 30, 2015  (FR) ..................... 15 60415

(51) Int. Cl.
  *C12M 3/00*    (2006.01)
  *C12M 1/00*    (2006.01)
  *C12M 1/42*    (2006.01)
  *C12N 13/00*   (2006.01)
(52) U.S. Cl.
  CPC ............ *C12M 35/02* (2013.01); *C12M 35/00* (2013.01); *C12M 35/04* (2013.01); *C12N 13/00* (2013.01)

(58) Field of Classification Search
  CPC ............................. C12M 35/00; C12M 35/04
  See application file for complete search history.

(56) References Cited

U.S. PATENT DOCUMENTS 5,153,136 A * 10/1992 Vandenburgh ......... C12M 25/04
                                                   435/286.1
5,217,899 A    6/1993  Shapiro et al.
(Continued)

FOREIGN PATENT DOCUMENTS

AU    2012201290 A1    9/2013
EP    2 747 452 A1     6/2014
(Continued)

OTHER PUBLICATIONS

Extended European Search Report dated Mar. 29, 2017 in Patent Application No. 16196122.2.
(Continued)

*Primary Examiner* — Nathan A Bowers
(74) *Attorney, Agent, or Firm* — Oblon, McClelland, Maier & Neustadt, L.L.P.

(57) ABSTRACT

A device for treating at least one biological cell includes at least one treatment support comprising a receiving surface enabling the adhesion of the at least one biological cell, at least one actuator capable of deforming said support in order to apply a stress to said at least one cell, and means of controlling said at least one actuator such that the actuator deforms the treatment support according to a given amplitude of deformation and for a given duration so as to generate at least one transitory pore in a membrane of the biological cell.

24 Claims, 11 Drawing Sheets

(56) References Cited

U.S. PATENT DOCUMENTS

| | | | | |
|---|---|---|---|---|
| 6,107,081 | A * | 8/2000 | Feeback | A61B 5/1108 |
| | | | | 435/284.1 |
| 8,304,228 | B2 * | 11/2012 | Fuhr | C12M 33/02 |
| | | | | 435/286.1 |
| 8,323,955 | B1 * | 12/2012 | Okandan | G01N 33/48728 |
| | | | | 435/173.1 |
| 2004/0235153 | A1 | 11/2004 | Takagi et al. | |
| 2007/0025919 | A1 | 2/2007 | Deem et al. | |
| 2007/0178584 | A1 * | 8/2007 | Naruse | C12M 23/26 |
| | | | | 435/289.1 |
| 2009/0088342 | A1 * | 4/2009 | Moraes | C12M 23/16 |
| | | | | 506/12 |
| 2009/0209035 | A1 * | 8/2009 | Watanabe | A61F 2/062 |
| | | | | 435/395 |
| 2010/0003282 | A1 | 1/2010 | Deem et al. | |
| 2010/0233799 | A1 * | 9/2010 | Takayama | B01L 3/50273 |
| | | | | 435/305.2 |
| 2012/0029261 | A1 | 2/2012 | Deem et al. | |
| 2012/0100602 | A1 | 4/2012 | Lu et al. | |
| 2012/0219981 | A1 * | 8/2012 | Muthiah | B29C 55/04 |
| | | | | 435/29 |
| 2013/0303948 | A1 | 11/2013 | Deem et al. | |
| 2015/0004077 | A1 | 1/2015 | Wikswo et al. | |
| 2015/0101418 | A1 * | 4/2015 | Campbell | G01N 3/08 |
| | | | | 73/826 |
| 2015/0150625 | A1 | 6/2015 | Deem et al. | |
| 2017/0072176 | A1 | 3/2017 | Deem et al. | |
| 2017/0175139 | A1 * | 6/2017 | Wu | C12M 35/00 |

FOREIGN PATENT DOCUMENTS

| | | |
|---|---|---|
| WO | WO 2013/18581 | 12/2013 |
| WO | WO 2015/148842 A1 | 10/2015 |

OTHER PUBLICATIONS

French Preliminary Search Report dated Jul. 1, 2016 in French Application 15 60415, filed on Oct. 30, 2015 ( with English Translation of Categories of Cited Documents).

U.S. Appl. No. 14/915,749, filed Mar. 1, 2016, 2016/0205478 A1, Fabrice Casset et al.

U.S. Appl. No. 15/046,803, filed Feb. 18, 2016, 2016/0244715 A1, Fabrice Casset et al.

U.S. Appl. No. 15/057,708, filed Mar. 1, 2016, 2016/0269827 A1, Fabrice Casset.

Suryanarayana A.N. Prasad et al. "Analytical Electroacoustic Model of a Piezoelectric Composite Circular Plate", AIAA Journal, vol. 44, No. 10, 2006, 8 pages.

F. Casset et al. "Piezoelectric membrane actuator design", $12^{th}$ Int. Conf. on Thermal Mechanical and Multiphysics Simulation and Experiments in Microelectronics and Microsystems (IEEE Eurosime), 2011, 3 pages.

Shinya Yoshida et al. "Fabrication and characterization of laterally-driven piezoelectric bimorph MEMS actuator with sol-gel-based high-aspect-ratio PZT structure", Journal of Micromechanics and Microengineering, 2013, 12 pages.

Armon Sharei et al. "A vector-free microfluidic platform for intracellular delivery", PNAS, vol. 110. No. 6, 201, 6 pages.

\* cited by examiner

DEVICE FOR TREATING AT LEAST ONE BIOLOGICAL CELL, NOTABLY WITH A VIEW TO INTRACELLULAR DELIVERY

TECHNICAL FIELD AND STATE OF THE PRIOR ART

The present invention relates to a device for treating at least one biological cell with a view to a step of intracellular delivery.

In the field of biomedicine it is sought to be able to introduce for example macromolecules into biological cells, either with a therapeutic aim or within the scope of studies. This method is designated intracellular delivery.

The macromolecules may be DNA or small interfering RNA designated siRNA, or inorganic molecules such as quantum dots or nanoparticles used for therapeutic purposes, for example in the treatment of cancers or instead to carry out intracellular marking.

The cell plasma membrane is to a large extent impermeable to macromolecules and techniques have been developed to enable this intracellular delivery.

Certain techniques of intracellular delivery of macromolecules are based on the use of polymeric nanoparticles, liposomes, or a modification of the target molecule by the addition of a penetration peptide for example. These techniques are highly dependent on the cell type and are poorly suited to structurally heterogeneous materials such as proteins. Moreover, these techniques are based on the endosomal pathway of which the efficacy is erratic. The use of viral vectors poses the problem of the non-control of the chromosomic insertion and only enables the delivery of DNA or RNA.

Physical techniques also exist, of electroporation by electric field or sonoporation type, which causes the appearance of pores in the plasma membrane by application of an electric field. Such techniques have the disadvantage of often having high cell mortality and may damage quantum dots for example.

Micro-injection, which is used in transgenesis, also exists but it does not make it possible to treat a large number of cells.

The document "*A Vector-free microfluidic platform for intracellular delivery*", A. Sharei et al., *PNAS*, Feb. 5, 2013, vol. 110, no 6, pages 2082-2087 describes a technique aiming to generate pores in the plasma membrane of the cell. To do so, the cells are in suspension in a liquid and the device comprises one or more contraction areas through which the cells are forced to pass. The diameter of the contraction areas are such that they apply shear and compressive stresses to the cells, which causes the appearance of temporary pores in the membrane. The opening of these pores makes it possible to introduce elements into the cells. These pores then re-close.

This technique is interesting, however it cannot apply directly to adherent cells. It would be necessary to apply to them beforehand mainly an enzymatic treatment which would modify their physiology. Moreover, the stresses applied to the cells and the time during which these stresses are applied, are not properly managed.

DESCRIPTION OF THE INVENTION

It is consequently an aim of the present invention to offer a device for treating at least one cell, for example with a view to intracellular delivery, not having the drawbacks of devices of the prior art.

The aforementioned aim is attained by a device implementing a treatment support on which biological cells are intended to adhere, and controllable means for deforming the treatment support so as to apply a mechanical stress to the cells, and in particular to their plasma membrane. This stress may be sufficient to cause the appearance of at least one transitory pore in the plasma membrane.

In the present application, "transitory pore" is taken to mean an opening that forms in the plasma membrane through application of a mechanical stress, of this membrane, the pore closing by itself after a certain time, unlike a definitive pore resulting from a disruption of the cell.

Thanks to the invention, the deformation of the cell is managed, since the type of stress and the level of stress applied to the cells and the application time of this stress are managed by controlling the deformation means.

In a very advantageous example, the formation of pores is managed.

In the case of an application to cellular delivery, the device according to the invention enables a cellular delivery not dependent on the endocytic pathway.

For example, the controllable means may be of the piezoelectric, electrostatic, magnetic or thermal actuator type.

Thanks to the device according to the invention, the mortality rate of the biological cells treated is substantially reduced compared to techniques of the prior art, such as electroporation. It may thus be used for therapeutic purposes.

The device according to the invention makes it possible to maintain over time a stress on the cell for example for the study of the mechanical response for example by atomic force microscopy. This type of study proves to be of great importance notably in the study of cancerous cells.

This device is moreover particularly suited to the treatment of cells such as human macrophages, human dendritic cells since these are naturally adherent. The treatment of these cells is very interesting because the modification of these cells by intercellular delivery is a major challenge in the immunotherapy field, all the more so given that intracellular delivery for these cells is particularly difficult with traditional techniques.

In a very advantageous manner, the device is a microelectromechanical system (MEMS) and or nanoelectromechanical system (NEMS) device, which makes it even more suited to the treatment of biological cells.

The subject matter of the present invention is then a device for treating at least one biological cell comprising:
- at least one treatment support comprising a receiving surface enabling the adhesion of said at least one biological cell,
- at least one actuator capable of deforming said support in order to apply a stress to said at least one cell, and
- means of controlling said at least one actuator such that the actuator deforms the treatment support according to a given amplitude of deformation and for a given treatment duration so as to apply said stress to the cell for said treatment duration.

In the present application, "treatment" is taken to mean the fact of modifying the biological cell by deformation thereof during the application of a mechanical stress. This deformation makes it possible to generate at least one pore in the cell and/or to determine the mechanical response of the cell to the stress notably to characterise it and in particular to discriminate cells such as cancerous cells.

The amplitude of deformation very advantageously makes it possible to generate at least one transitory pore in a membrane of the biological cell so as to treat said cell and/or the amplitude of deformation may make it possible to determine the mechanical response of the cell to the stress so as to characterise it.

Another subject matter of the present invention is a microfluidic cellular delivery device comprising at least one treatment device according to the invention, means of supplying a solution comprising at least one biological cell to treat and means of evacuating the fluid.

Another subject matter of the present invention is a method of cellular delivery implementing the microfluidic cellular delivery device according to the invention, comprising the steps of:
- placing the solution containing the at least one biological cell to treat in contact with the treatment support,
- adhesion of said at least one cell to the treatment support,
- supplying a solution containing the elements to introduce into the cell,
- applying a stress to the cell to cause the appearance of at least one transitory pore in the membrane of the cell by deformation of the treatment support,
- stopping the application of the stress,
- closing the at least one transitory pore,
- evacuating the cell.

BRIEF DESCRIPTION OF THE DRAWINGS

The present invention will be better understood on the basis of the description that follows and the appended drawings in which.

DETAILED DESCRIPTION OF PARTICULAR EMBODIMENTS

Figure 1:
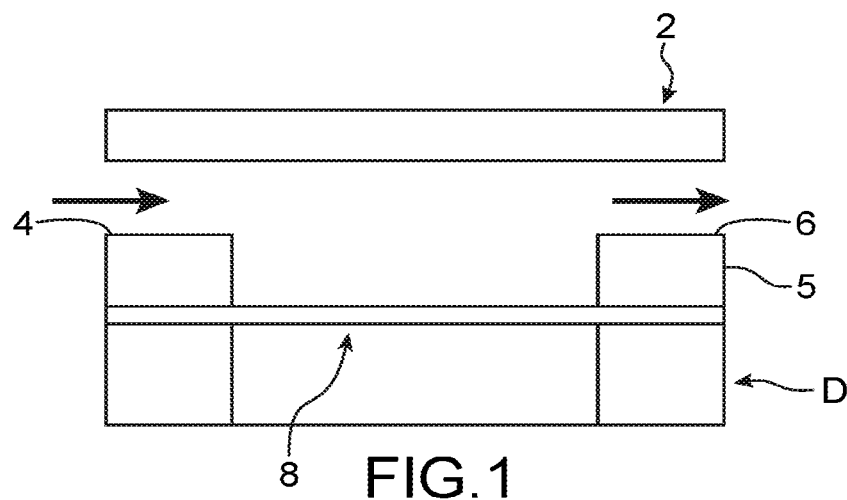
FIG. 1 is a general schematic representation of an example of embodiment of a treatment device according to the invention.

In FIG. 1 may be seen a schematic representation of an example of a treatment device implementing the present invention. The treatment device makes it possible to apply a stress to the cell, for example to generate one or more pores in the membrane of the cell, these pores enabling for example the delivery of given elements to the cell, but not exclusively.

In the example represented, the treatment device comprises a casing 2 provided with a fluid supply inlet 4 produced in a lateral wall 5 of the casing and a fluid evacuation outlet 6 produced in the lateral wall 5 of the casing and a bottom 8. The supply inlet 4 and the evacuation outlet 6 are arranged with respect to the bottom 8 such that the flux of fluid flows on the bottom from the inlet 4 to the outlet 6.

The bottom 8 is formed by a device capable of deforming the biological cells that have adhered thereto.

Figure 2:
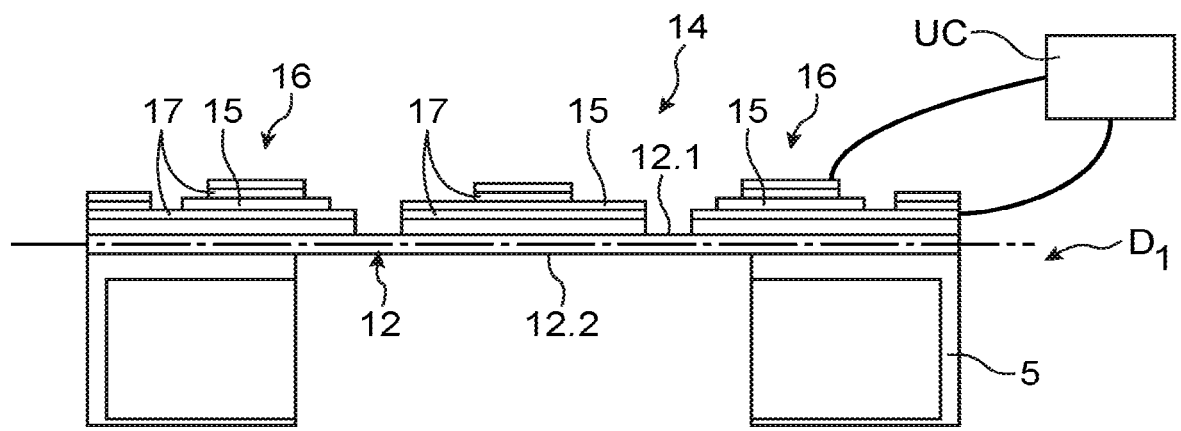
FIG. 2 is a sectional view of an example of a treatment device provided with controllable deformation means of piezoelectric type capable of being implemented in the device of FIG. 1.

In FIG. 2 may be seen an example of embodiment of the device D1 capable of deforming biological cells that have adhered thereto implementing piezoelectric means.

The device D1 comprises a treatment support 12, in the example represented, formed by a thin wafer suspended from the lateral wall of the casing and capable of deforming elastically. The treatment support forms in this example the casing bottom. The device D1 also comprises at least one actuator capable of deforming the treatment support 12 in an out-of-plane direction. In the example represented, the device comprises two actuators 14, 16 implementing a ferroelectric material, for example PZT, one of the actuators serves for the displacement of the membrane upwards and the other actuator serves for the displacement of the membrane downwards. In the case where a piezoelectric material is implemented, a single actuator is sufficient to assure the upwards and downwards displacements, since a piezoelectric material expands and contracts depending on the sign of the voltage applied.

The treatment support 12 has a circular shape, the actuator 14 is a ferroelectric actuator and is arranged substantially at the centre of the treatment support 12 on one face 12.1 opposite to that 12.2 situated in the casing and intended to enter into contact with the fluid. The actuator 16 is also a ferroelectric actuator of annular shape and bordering the outer edge of the outer surface 12.1 of the membrane 12.

The actuators 14 and 16 are connected to a control unit UC making it possible to control the actuators so that they cause a deformation of the treatment support according to a given amplitude and for a given time.

The inner surface 12.2 is such that it enables the adhesion of the cells that it is wished to treat. The surface 12.2 is for example made of glass, silicon or any semiconductor material.

In an advantageous manner, the surface of the treatment support 12 may be functionalised to delimit one or more preferred areas of adhesion of the cell or cells.

For example, the functionalisation of the membrane is obtained by a deposition or coating, for example of molecules of the extracellular matrix, for example molecules of fibronectin or laminin, or by chemical fixation of specific antibodies of studied cell type. The functionalisation deposition is for example a chemical deposition which is carried out by exposing the surface to treat to a solution containing the molecules to deposit and attaining the adsorption of these molecules on the surface of the membrane.

In a variant, it is possible to form localised areas of material on the treatment support, for example of nitride or oxide type, favouring the adhesion of the cells during the method of microelectronic production of the membrane. For example, a layer of this material is formed on the layer intended to form the membrane and the adhesion areas are determined by photolithography and etching.

It will be understood that it is possible to deposit a material that conversely reduces, or even prevents, the adhesion of the cells to delimit areas where adhesion is not favoured, the cells adhering between these areas.

It may be provided in addition or instead to treat the cells to favour their adhesion to a certain material for example by fixing on the treatment support elements which for their part offer good adhesion with the material of the treatment support.

In a variant, it could be envisaged that it is the side of the device bearing the actuator or actuators that enables the adhesion of cells; means of electrically insulating the actuators from the fluid containing the cells could then be provided, for example an electrically insulating layer.

This functionalisation applies to all the examples that are described in the remainder of the description.

The actuators 14, 16 comprise a ferroelectric or piezoelectric material 15 and two electrodes 17 on either side of the material 15 making it possible to apply to this material 15 an electric field on command, which causes a deformation in the plane of the material and thus an out-of-plane deformation of the membrane with which it is integral, by bi-metal effect.

The optimisation of such actuators is described in the document F. Cosset et al., "*Piezoelectric membrane actuator design*", 12*th Int. Conf. On Thermal, Mechanical and Multiphysics Simulation and Experiments in Microelectronics and Microsystems* (*IEEE Eurosime*), 18-20 Apr. 2011, pp. 1-5.

In a variant, the membrane could have any other shape, for example be of square or rectangular shape.

In a variant, a single actuator could be implemented.

Figure 3B:
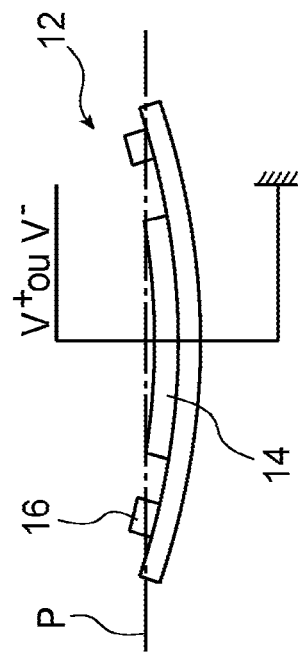
FIG. 3A is a top view represented schematically of the treatment support implemented in the device of FIG. 2, FIGS. 3B and 3C are sectional views along the plane A-A of the treatment support of FIG. 3A in two different states.
Figure 3C:
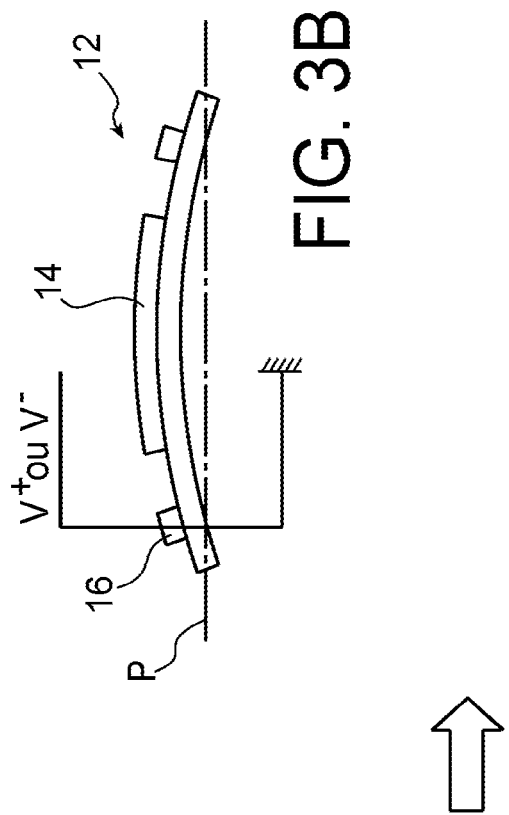
Figure 3A:
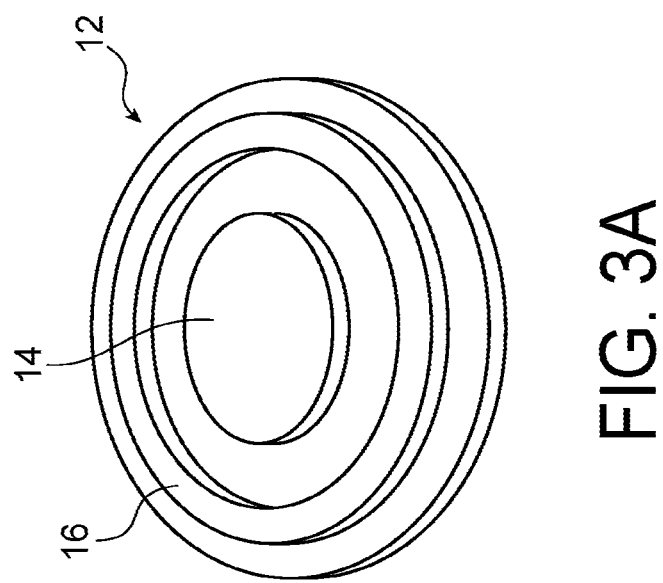

In FIGS. 3A to 3C may be seen the treatment support of FIG. 2 seen from above and the device in two deformation states.

In FIGS. 3A to 3C, only the membrane is represented with the actuators.

In the example represented, the application of a voltage on the actuator 16 causes a displacement of the treatment support 12 upwards. The application of a voltage on the actuator 14 causes a displacement of the membrane 12 downwards.

In another example of embodiment, the actuators are produced from piezoelectric materials such as for example AlN, ZnO, etc. An out-of-plane electric field, in the same sense as the polarisation in the material, is going to induce an extension in the plane of the piezoelectric material. Conversely, an out-of-plane electric field, inversed with respect to the polarisation of the material, is going to induce a contraction in the plane of the piezoelectric material. Thus upwards and downwards displacements may be obtained using a single actuator. The amplitude of the displacement of the membrane is proportional to the voltage applied to the terminals of the actuators.

Figure 4:
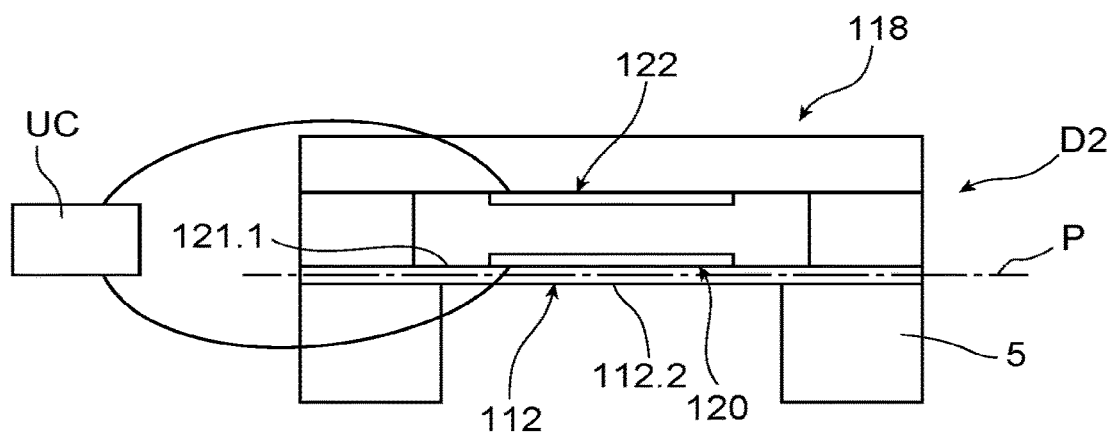
FIG. 4 is a schematic sectional view of an example of a treatment device provided with controllable deformation means of electrostatic type capable of being implemented in the device of FIG. 1.

In FIG. 4 may be seen another example of device D2 capable of deforming biological cells that have adhered on the treatment support, said device implementing electrostatic means.

The device comprises a fixed part 118 and a treatment support 112 suspended on the fixed part 118. The electrostatic means, making it possible to deform the treatment support 112, comprise at least one first electrode 120 borne by one support treatment face 112.1 opposite to the face 112.2 on which the cells are intended to adhere and at least one second electrode 122 on the fixed part 118 facing the first electrode 120. The first 120 and second 122 electrodes are connected to a voltage or current source (not represented), which is controlled by the control unit UC.

The treatment support is for example made of polysilicon or any other semiconductor material.

When a voltage difference is applied between the electrodes 120 and 122, an electric field appears between the electrodes and causes an attraction or a repulsion of the first electrode with respect to the second electrode 120 and thus a displacement of the treatment support 112 which, on account of its anchoring on the fixed part, deforms.

According to another example of embodiment, not represented, the device capable of deforming the biological cells adhering thereto may comprise one or more thermal actuators.

The operation of a thermal actuator is similar to that of a piezoelectric actuator. A current flows through the thermal actuator which is integral with the membrane, the current causes an increase in the temperature of the actuator by Joule effect. This increase in temperature induces a thermal expansion causing a mechanical torque deforming the membrane. In this example of embodiment, it is advantageously possible to provide means of controlling the temperature of the liquid of the cells to avoid an increase in temperature which could be detrimental to the cells. For example it is possible to provide to cool the liquid medium in a controlled manner.

According to another example of embodiment not represented, the device capable of deforming the biological cells adhering thereto may comprise one or more magnetic actuators. Compared to an electrostatic actuator, the electrode integral with the membrane is replaced by a magnetic material and means capable of generating a magnetic field to attract or to repel the magnetic material are provided. The treatment support is then deformed along the magnetic field generated.

The operation of the device of FIG. 2 will now be described.

When one or more cells have adhered on the treatment support, this is deformed by the deformation means. To do so, a continuous voltage is applied to the deformation means, for example to the electrodes 17 of the piezoelectric actuators. The cell or cells arranged on the support are then also deformed. The deformation may be sufficient to cause the generation of one or more pores in the plasma membrane. The value of the voltage applied to the electrodes has been determined to cause a deformation of the cell and the appearance of pores but to avoid complete disruption of the membrane. Alternatively, the stress applied to the membrane deforms the cell without generating pores.

Figure 5A:
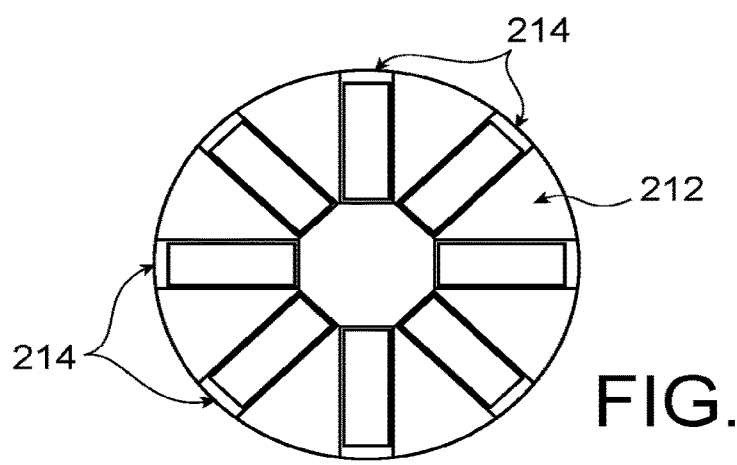
FIG. 5A is a top view of another example of embodiment of a treatment support provided with controllable deformation means of piezoelectric type.
Figure 5B:
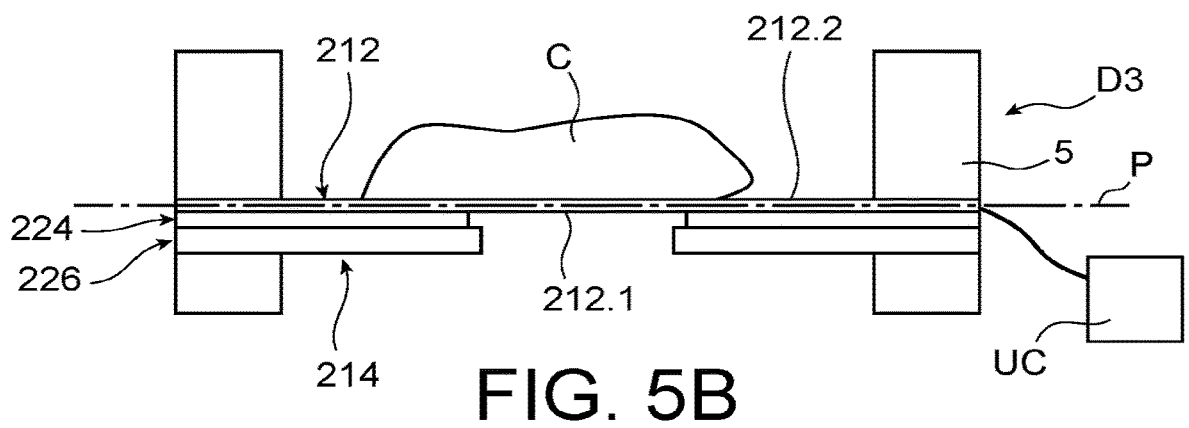
FIGS. 5B and 5C are sectional views along the plane B-B of a treatment device implementing the treatment support of FIG. 5A integrated in a treatment device in a state not applying a deformation and a state applying a deformation respectively.
Figure 5C:
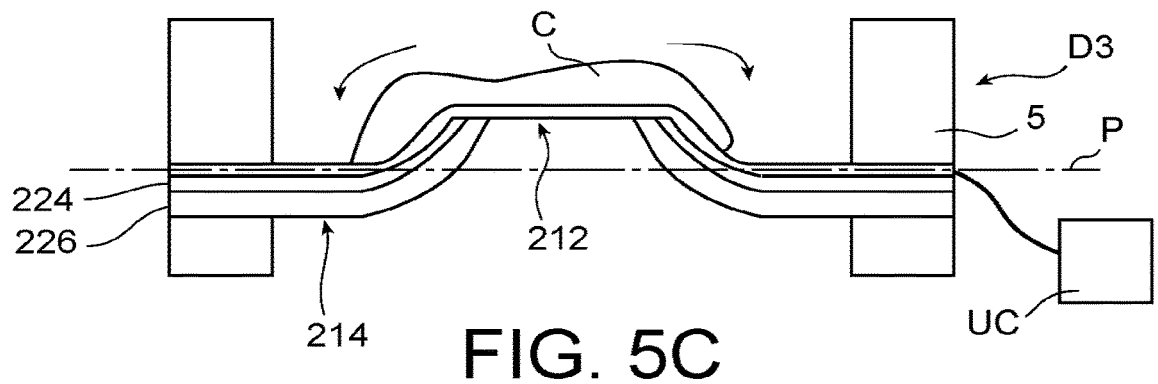

In FIGS. 5A to 5C may be seen another example of embodiment of a treatment device D3 offering amplified deformation compared to the device of FIGS. 2 and 3A to 3C The device comprises a flexible treatment support 212, for example made of synthetic material, of polymer type. "Flexible support" is taken to mean a support having low rigidity on account of its low Young's modulus, comprised between several hundreds of MPa to ten or so GPa. For example the support is made of polycarbonate, polyethylene naphthalate, etc.

In the example represented, the treatment support 212 has a disc shape and is fixed at the level of its outer periphery between the wall 5 of the device confining the medium of the cells and the actuators. The face 212.2 of the treatment support that forms the upper face of the treatment support in the representation of FIG. 5A is that on which the cells are going to adhere. The device also comprises several piezoelectric actuators 214 spread out under the treatment support each comprising a fixed-free element 224 made of piezoelectric material arranged under the treatment support and in contact with its lower face 212.1 and electrodes (not represented) on either side of the element to apply to it a control voltage. The elements 224 are fixed by their radially outer end and are free at the level of their radially inner end. Each actuator 214 is associated with a fixed-free beam 226 superposed on the element 224 and integral in movement therewith. The beam 226 is such that it is deformable in flexure under the action of the actuator 214. The beams 226 are fixed by their radially outer end and are free at the level of their radially inner end.

In the example represented, the device comprises several actuator-beam assemblies spread out in a star shape under the treatment support in a uniform manner. The implementation of beams makes it possible to increase the amplitude of deformation of the flexible treatment support 212 on account of their reduced rigidity compared to the support. The beams thus make it possible to increase the deformation of the membrane and thus the tangential stresses applied in the plane of the membrane The operation of this device is the following. In the absence of voltage applied to the actuators 214, the treatment support 212 is substantially flat and the cell C is not deformed (FIG. 5B).

When a voltage is applied to each of the actuators 214, the piezoelectric elements 224 deform, deforming the beams 226 which bend causing the deformation of the treatment support 212 and thus of the cell C that has adhered thereto (FIG. 5C).

This embodiment makes it possible to amplify the deformation undergone by the cell C compared to that applied by the device of FIG. 2.

The treatment supports and the associated deformation means described in relation with FIGS. 1 to 5C assure a spherical deformation of the cell, i.e. an axisymmetric deformation, as is shown schematically in FIG. 5C.

The device of FIG. 5A could nevertheless be controlled to apply a non-axisymmetric stress, for example by activating a single actuator 214 or by activating a pair of aligned actuators 214 or several pairs of aligned actuators 214 so as to apply a stress along one or more favoured axes.

Furthermore, a device similar to that of FIG. 5A but only comprising one actuator or one or more pairs of actuators does not go beyond the scope of the present invention.

Moreover, it may be envisaged to apply to one or certain actuators a positive voltage and to one or other actuators a negative voltage so as to cause a deformation of the membrane on the two sides of the plane of the membrane at rest. Moreover, it is possible to provide not to apply the same voltage to all the actuators such that different levels of deformation are applied to the membrane.

It will be understood that the actuators of the device of FIG. 5A may be replaced in all or part by thermal, electrostatic, magnetic actuators, etc.

In FIGS. 6A to 7B may be seen another example of device making it possible to apply a cylindrical deformation to the cell, i.e. a deformation around an axis.

Figure 6A:
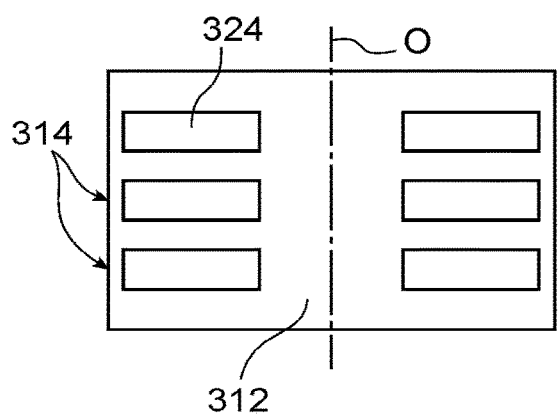
FIGS. 6A and 6B are top and transversal sectional views respectively of an example of embodiment of a treatment support capable of applying a cylindrical deformation to a cell.
Figure 6B:
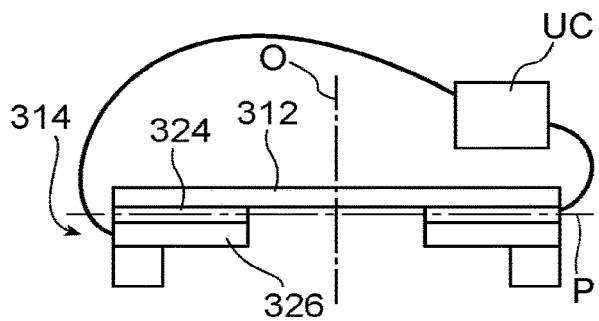
Figure 8:
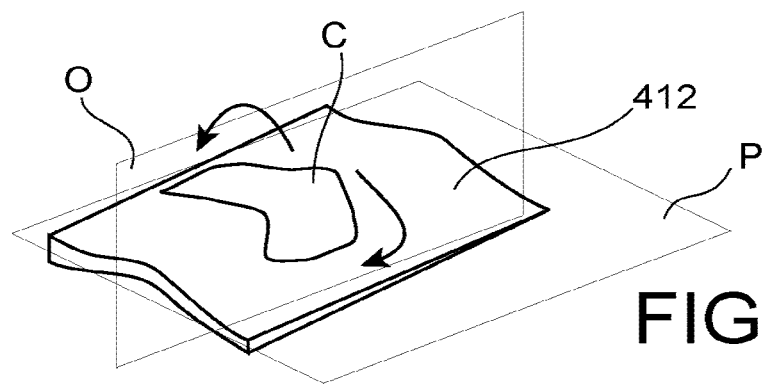
FIG. 8 is a schematic representation of a cell undergoing a cylindrical deformation.

The device of FIGS. 6A and 6B is of the same type as that of FIG. 5A, it comprises piezoelectric elements 324 and fixed-free beams 326 under a treatment support made of flexible material 312, for example made of polymer material. In the example represented, the treatment support 312 is of rectangular shape and the actuators 314 are spread out on either side of a plane of symmetry O of the treatment support 312 orthogonal to the median plane of the membrane. Thus, when a same voltage is applied to the actuators 314, the treatment support sees its central area along the plane of symmetry O displaced from one side to the other of the median plane as is represented in FIG. 8. In the example represented and in an advantageous manner, the actuators 314 are spread out in a symmetrical manner on either side of the plane O making it possible to apply a cylindrical deformation to the cell.

In a variant, it could be envisaged that the actuators are not arranged in a symmetrical manner with respect to the plane O. It could then be provided to only actuate the actuators positioned symmetrically with respect to the plane O, if it is wished to apply a cylindrical deformation to the cell.

Figure 7A:
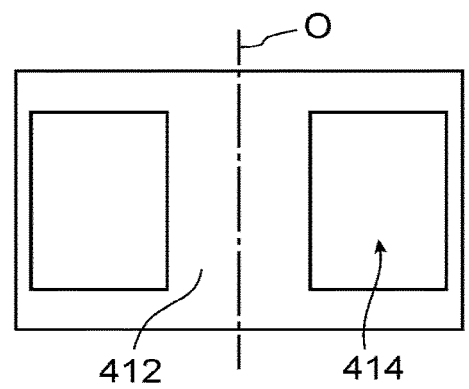
FIGS. 7A and 7B are top and transversal sectional views respectively of another example of embodiment of a treatment support capable of applying a cylindrical deformation to a biological cell.
Figure 7B:
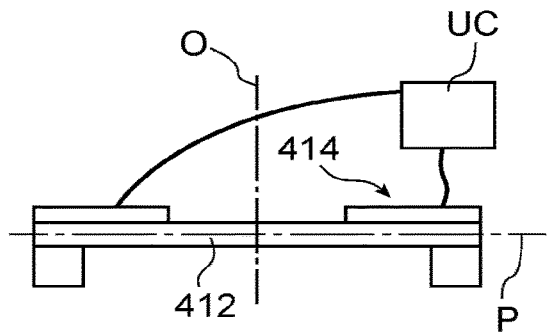

The device of FIGS. 7A and 7B is of the same type as that of FIG. 2. In the example represented, the treatment support 412 is of rectangular shape and the actuators 414 are spread out on either side of a plane of symmetry O of the treatment support 412 orthogonal to the median plane of the treatment support. Thus when a same voltage is applied to the actuators, the central area of the treatment support 412 along the plane of symmetry O is displaced from one side to the other of the median plane as is represented in FIG. 8. As for the device of FIGS. 6A and 6B, the actuators 414 are spread out in a symmetrical manner on either side of the plane O, but this is in no case limiting, they could for example be arranged in staggered rows or in any other manner.

Figure 9A:
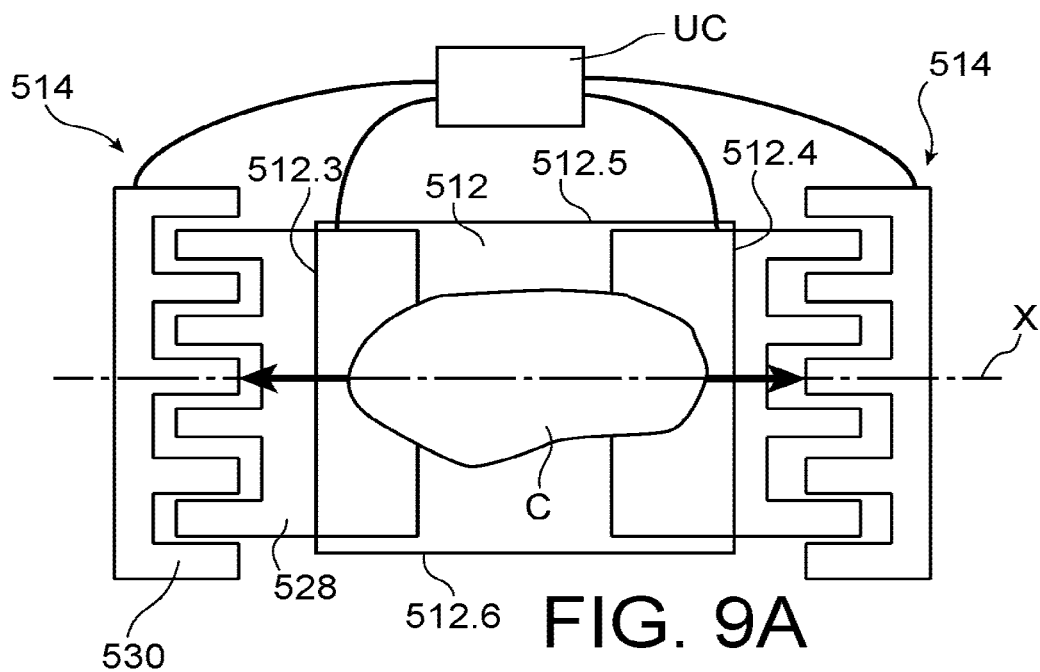
FIGS. 9A and 9B are top and transversal sectional views respectively of a treatment support with electrostatic actuation capable of applying a uniaxial deformation to the biological cell.
Figure 9B:
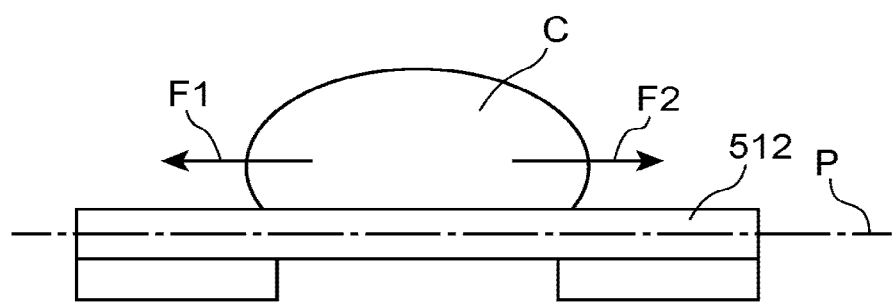

In FIGS. 9A and 9B may be seen another example of device implementing electrostatic actuators.

The device comprises a flexible treatment support 512, for example made of synthetic material, such as a polymer. In the example represented, the treatment support 512 is of rectangular shape. The device also comprises two actuators 514, each arranged at the level of two edges 512.3, 512.4 opposite to the membrane along an axis X.

The two actuators are of similar structures, only one of the actuators will be described in detail.

The actuator is of the interdigitated comb type. It comprises a fixed comb 530 and a moveable comb 528 integral with the edge 512.3 of the treatment support 512.

The operation of the device is the following: when a voltage is applied between the fixed comb 530 and the moveable comb 528, the moveable comb moves closer to the fixed comb by electrostatic attraction. The edge of the treatment support integral with the moveable comb is displaced along the axis X towards the left in the representation of FIGS. 9A and 9B. This displacement is symbolised by the arrow F1. When the two actuators are supplied and when the two moveable combs move away from their associated fixed comb, the treatment support is stretched according to the arrows F1 and F2 in the plane P, and the cell C adhering to the treatment support 512 undergoes the same deformation. This device makes it possible to apply a uniaxial deformation to the cell.

In a variant, the actuator could only comprise one moveable comb interdigitated with a fixed comb, the support could then be anchored on the moveable comb on a fixed mechanical anchoring. The support could then be stretched by displacement of the moveable comb with respect to the mechanical anchoring. In this variant, the applicable stress would nevertheless be two times lower than that applicable with the device of FIG. 9A.

In a further variant, a single actuator could be provided. One edge of the treatment support could be integral with a fixed comb and the other edge could be integral with the moveable comb. When a voltage is applied between the two combs, the moveable comb moves away from the fixed comb taking with it the edge with which it is secured, applying a tensile force to the treatment support.

It may be envisaged to produce a device with several pairs of actuators, thus deformations along several axes may be applied. For example, it is possible to provide arranging a pair of actuators along an axis perpendicular to the axis X, the moveable combs being integral with the edges 512.5, 512.6. By actuating the different pairs of actuators simultaneously, an axisymmetric tensile stress may be applied to the cell.

In a variant, the electrostatic actuators could be replaced by piezoelectric actuators such as those described in the document Yoshida et al., "*Fabrication and characterization of laterally-driven piezoelectric bimorph MEMS actuator with sol-gel-based high aspect ratio PZT structure*", J. Micromech. Microeng. 23 (2013) 065014 (11pp). Such actuators comprise fixed-free beams deformable in the plane, comprising a silicon core perpendicular to the plane of the treatment support and layers of piezoelectric material on either side of the core and extending perpendicularly to the plane of the treatment support. The free ends of the beams are secured to one end of the treatment support. By providing such actuators at the level of two opposite edges of the treatment support, it is possible to apply a tensile force to the treatment support and to the cell that adheres to the treatment support.

As a practical illustration, estimated dimensioning values of the treatment support and the voltages to apply to form a pore in the plasma membrane of the cell are given below.

The order of magnitude of the linear voltage to create a pore in a biological cell is $1 \cdot 10^{-11}$ j/m. To create a pore of 100 nm diameter in the membrane of a cell of 5 µm to 10 µm diameter, the order of magnitude of the energy required is of the order of $1 \cdot 10^{18}$ J.

Let us consider the case of the device of FIG. 2 or the device of FIGS. 6A to 7B in which the deformation of the cell is obtained by imposing a radius of curvature with spherical symmetry or cylindrical symmetry respectively. It has been estimated that the order of magnitude of the radius of curvature of the treatment support is 3 µm to form a pore of 100 nm diameter or 10 µm to form a pore of 10 nm diameter. These are high values because these estimations concern the formation of definitive pores, i.e. which do not re-close. It is estimated that the radius of curvature to form transitory pores is of the order of $10^4$ µm and that this radius of curvature may be obtained by means of a treatment support of 600 µm diameter, this having a deformation of the order of 4.5 µm. Considering a piezoelectric actuator, a voltage of the order of 50 V will make it possible to obtain the required deformation of the treatment support. These dimensions and voltage values are compatible with microelectromechanical and/or nanoelectromechanical devices.

In the case where the cell is deformed by stretching as is the case with the devices of FIGS. 9A and 9B, it has been estimated that the displacement to apply is of the order of a tenth of a µm. As an example, it is possible to obtain around 4 µm deformation under 10V for a membrane of 800 µm radius.

The steps of using a device according to the invention to enable cellular delivery to a cell will now be described. The case of a single cell will be described, but it will be understood that in general several cells are treated simultaneously by the same device as a function of the size of the treatment support.

During a first step, the cell that it is wished to treat, i.e. to which a cellular delivery is to be applied, is introduced into the device via the supply inlet. The cell is in general in suspension in a liquid medium. For example a pipette is used that can dispense a volume of liquid and the desired quantity of cell. In a variant, a microfluidic circuit may be connected to the supply inlet and assure the circulation of the fluid containing the cells between a reservoir and the device.

During a second step, the cell adheres to the treatment support. To do so, a sedimentation phase takes place during which the cell is going to deposit by gravity on the treatment support. The cell then clings onto the membrane and adheres. The duration of this step may be of the order of several tens of minutes. The longer this step, the higher the intensity of the adhesion force. The control of the duration of this step thus makes it possible to control the adhesion force of the cell on the membrane.

As explained above, the surface of the support may comprise areas facilitating the adhesion of the cells or, quite the reverse, to make it more difficult. In this case the cell adheres in an area where adhesion is favoured or at least not deteriorated.

In a variant, it may be envisaged to use one or more templates above the surface of the support, the template or templates being made of a material which does not favour cellular adhesion and comprising orifices at the places where it is wished that the cells deposit. The template or the templates is or are then removed at the end of the sedimentation step.

During a following step, the medium containing the elements to introduce into the cell is injected into the device. This medium is for example a culture medium containing the macromolecules to introduce into the cell. This medium may be injected using a pipette or a fluidic circuit, which may be the same as that transporting the medium containing the cells. Advantageously, the medium containing the elements to introduce into the cell will be injected into the treatment device prior to the opening of the pores.

During a following step, a deformation is applied to the cell. To do so, the actuators are activated by applying a continuous actuating voltage to the terminals of the electrodes of the actuator. The actuator brings about the desired deflection of the support, applying a deformation to the cell that has adhered on the support. This deformation causes the appearance of at least one transitory pore. The duration of application of the stress to the cell is of the order of several seconds.

The choice of the voltage to apply to the actuators is made by the operator using for example abacuses giving the deflexion of the treatment support as a function of the voltage applied to produce one or more transitory pores in given types of cells that will have been produced during the manufacture of the device.

During a following step, the actuator is deactivated by cancelling the continuous voltage applied to the electrodes of the actuator, the treatment support recovers its position at rest and returns the adherent cell to a non-stressed state, the membrane of the cell comprises at least one pore.

As long as the pore or pores are open, the elements to introduce contained in the liquid medium penetrate into the cells via the pore or pores.

During a following step, no stress is applied to the cell to enable the closing of the pore or pores. This step may last several minutes.

At the end of the step of closing the pores, the treated cell is recovered. It is possible for example to provide to make the treatment support vibrate by means of the actuator or actuators and/or to apply an enzymatic treatment. These recovery techniques make it possible not to damage the cell. Then the cell may be recovered in the liquid using a pipette, or by a microfluidic circulation transferring the cells to a suitable receptacle. The cell may undergo several treatments to have delivered different types of elements.

As explained previously, this treatment device has the advantage of having a very low cell mortality rate compared to devices of the prior art.

The treatment device may comprise several separate treatment supports controllable in a separate or shared manner.

The density of cells that can adhere to a support depends on the cell type but as an example, an order of magnitude of this density may be of the order of 100 000 cells/cm$^2$.

An example of method of producing a treatment device according to the invention will now be described, said device comprising a circular treatment support. It is advantageously a method implementing microelectronic techniques, which makes it possible to produce a device suited to the size of cells. Other methods could be envisaged.

Figure 10A:
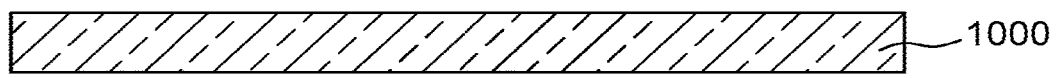
FIGS. 10A to 10S are schematic representations of the elements obtained during the different steps of an example of method of producing a treatment device, FIGS. 10N' to 10R' are schematic representations of the elements obtained during the different steps according to a variant of a method of producing a treatment device.
Figure 10B:
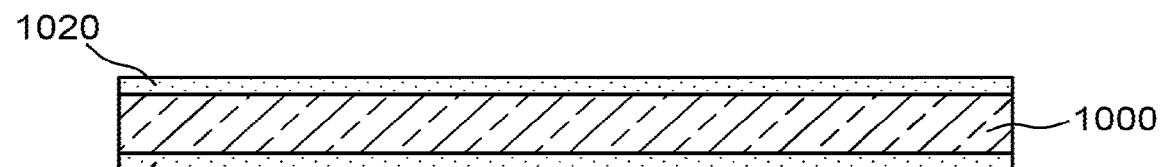
Figure 10C:
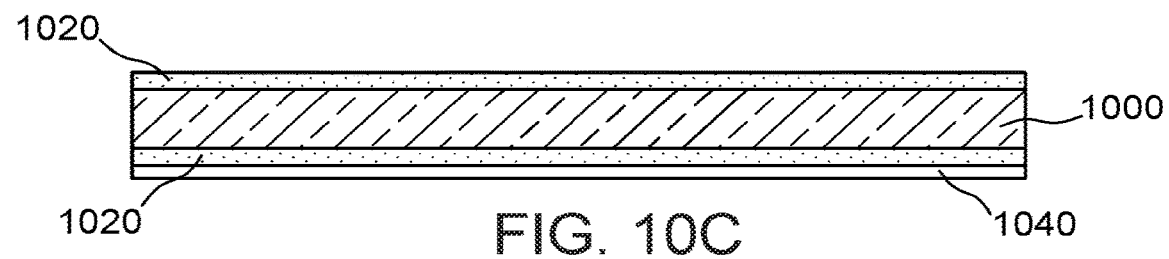
Figure 10D:
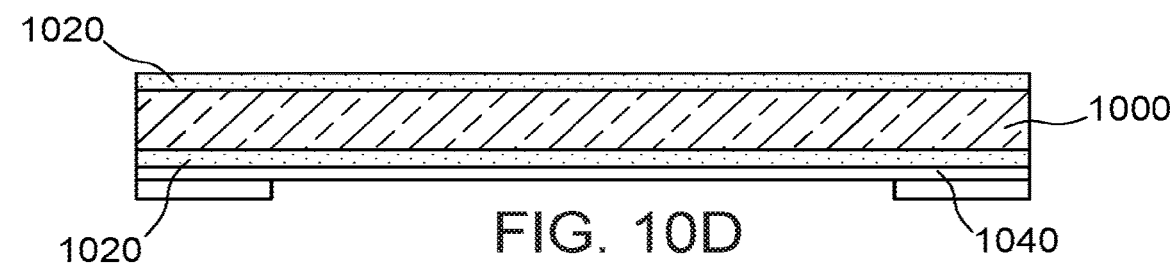
Figure 10E:
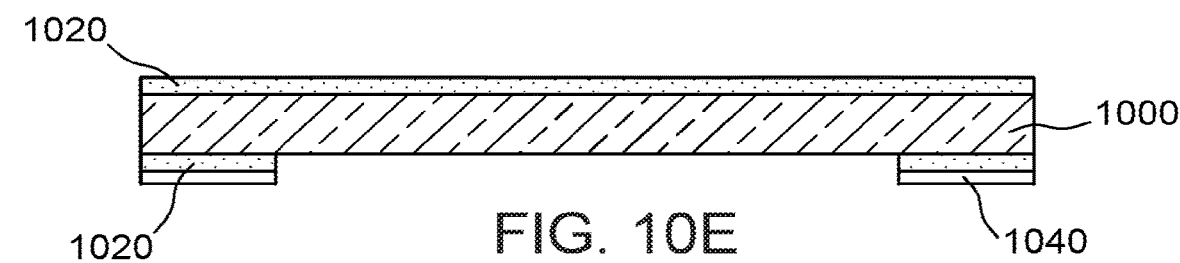
Figure 10F:
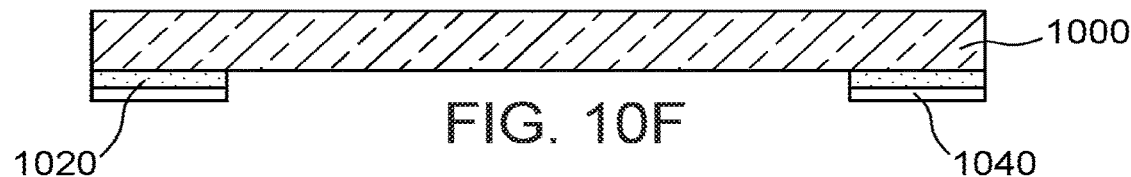
Figure 10G:
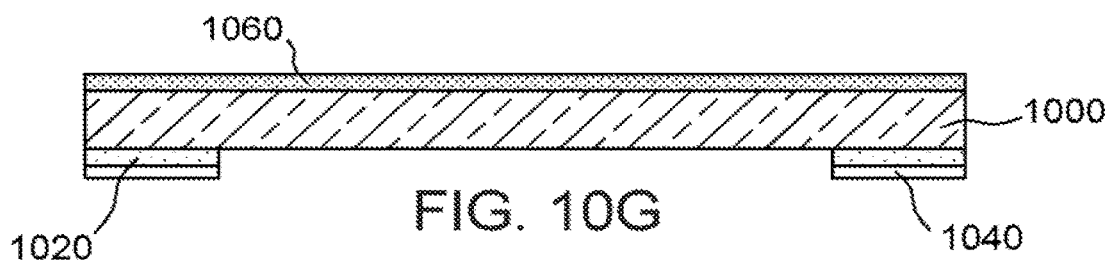
Figure 10H:
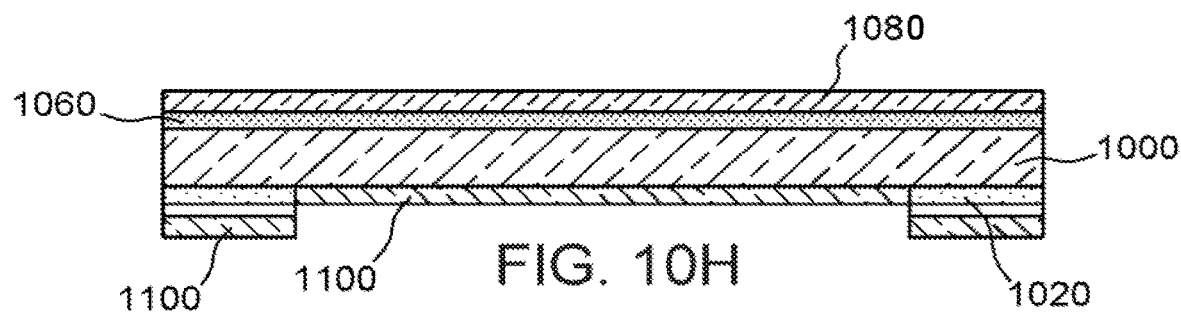
Figure 10I:
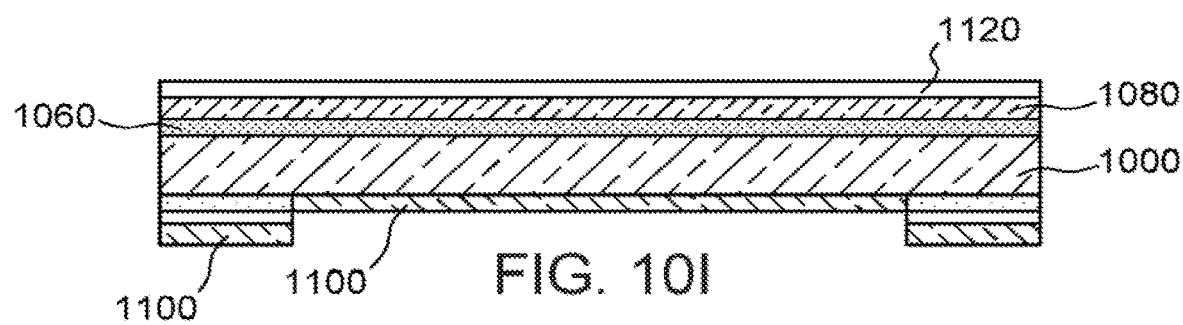
Figure 10J:
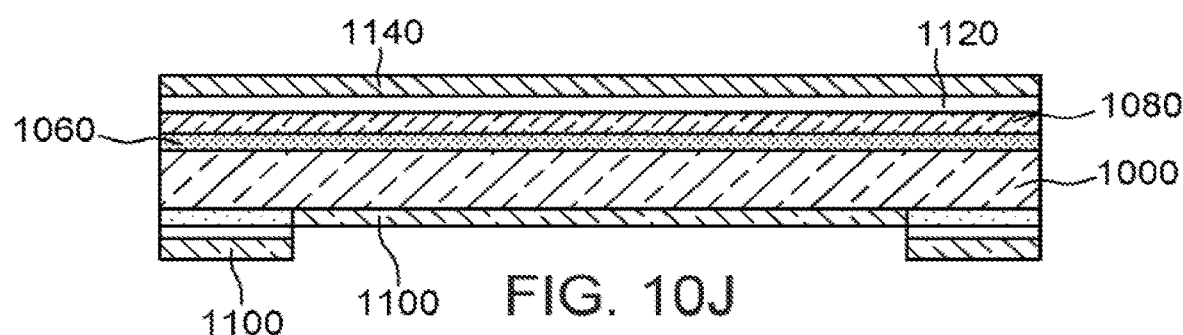
Figure 10K:
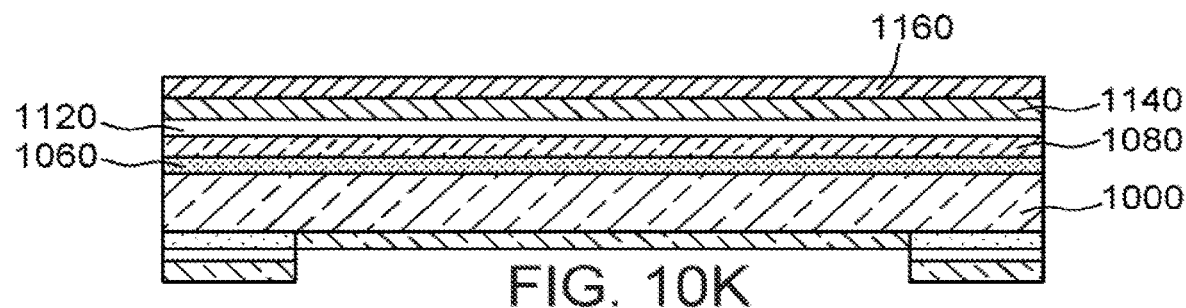
Figure 10L:
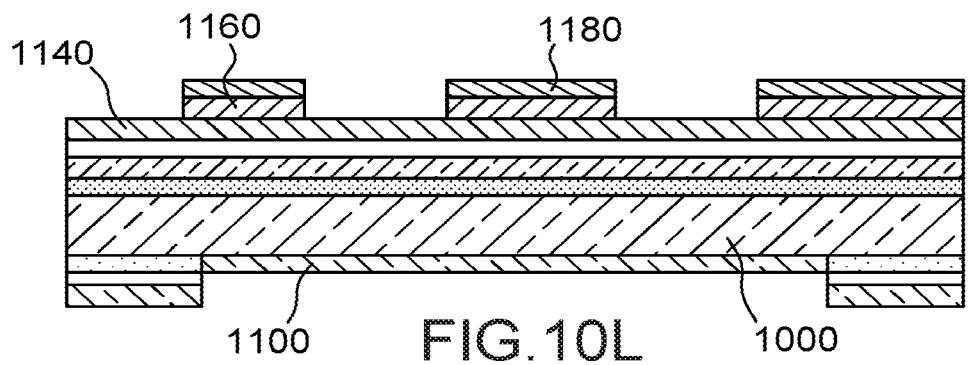
Figure 10M:
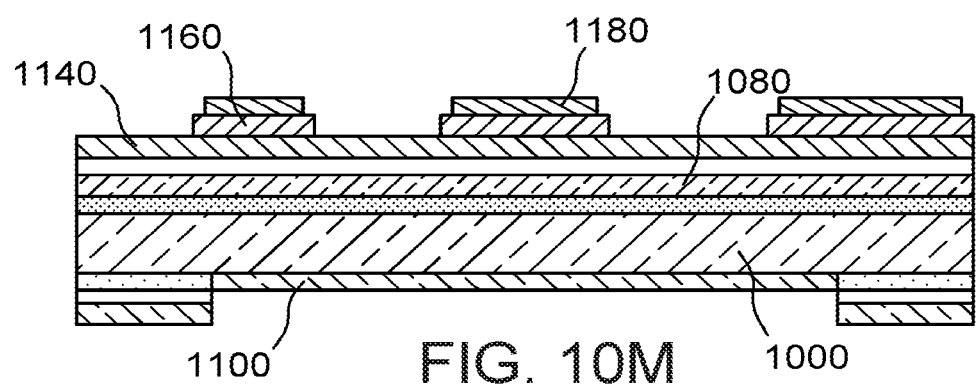
Figure 10N:
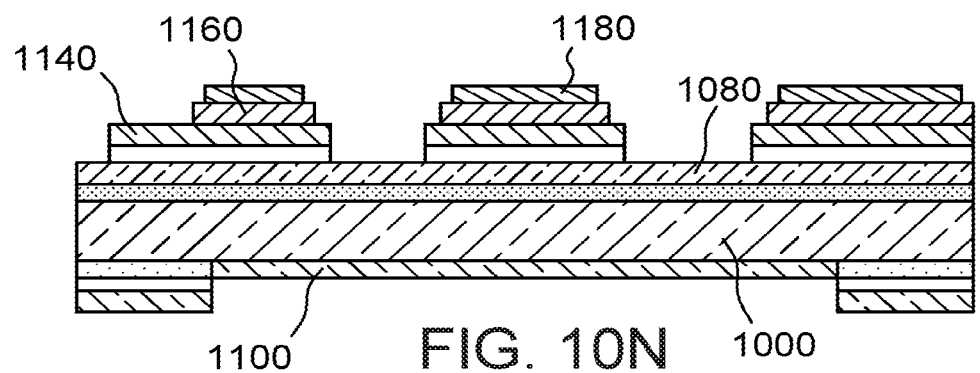
Figure 10O:
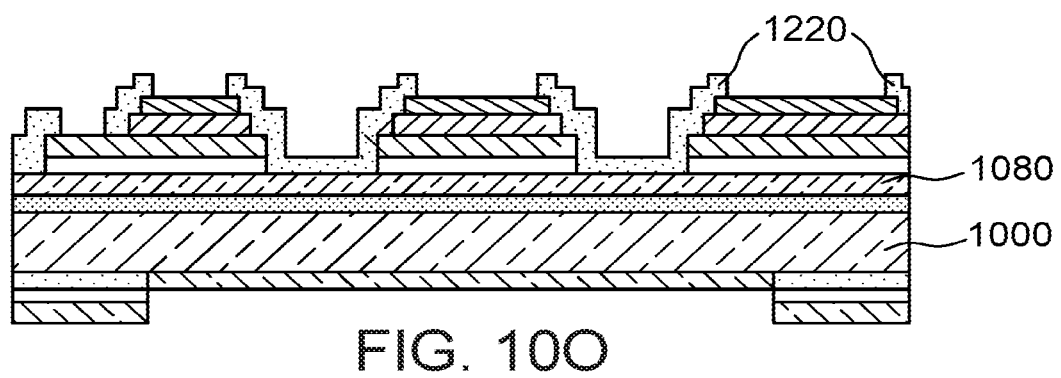
Figure 10P:
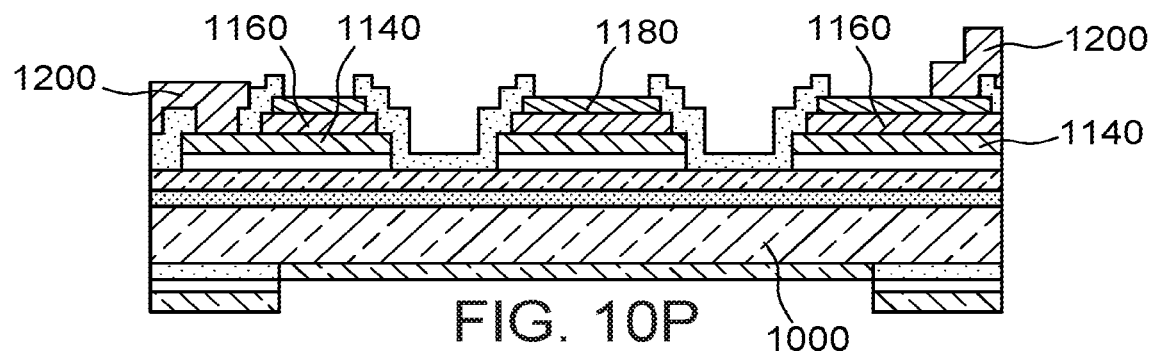
Figure 10Q:
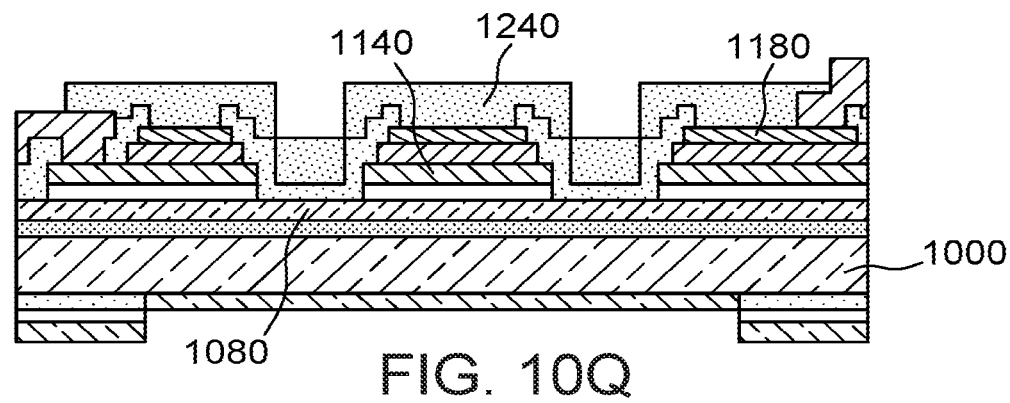
Figure 10R:
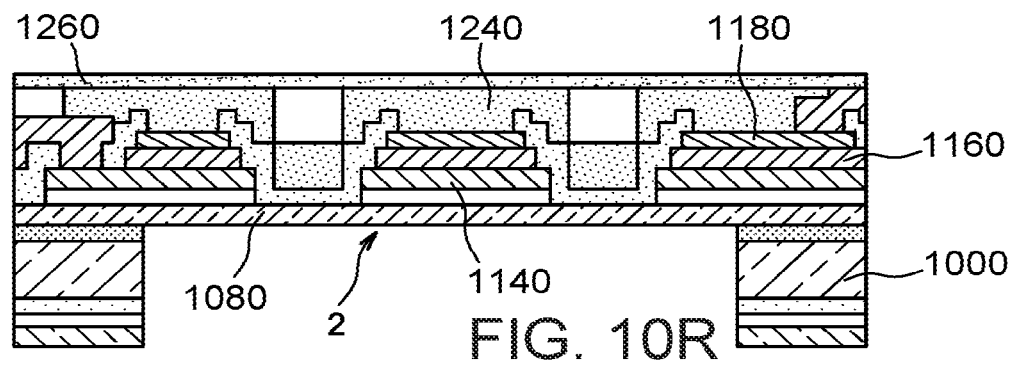
Figure 10S:
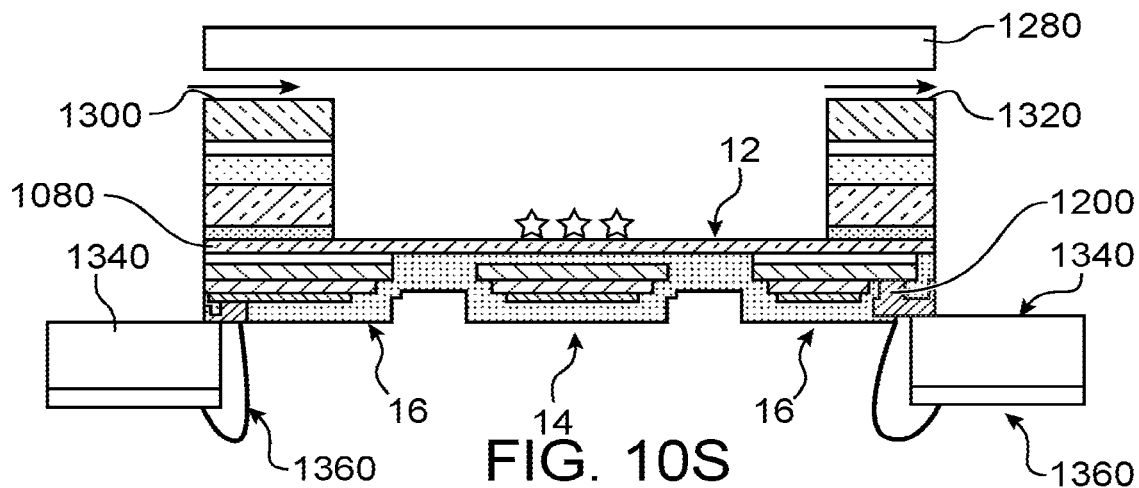
Figure 10N:
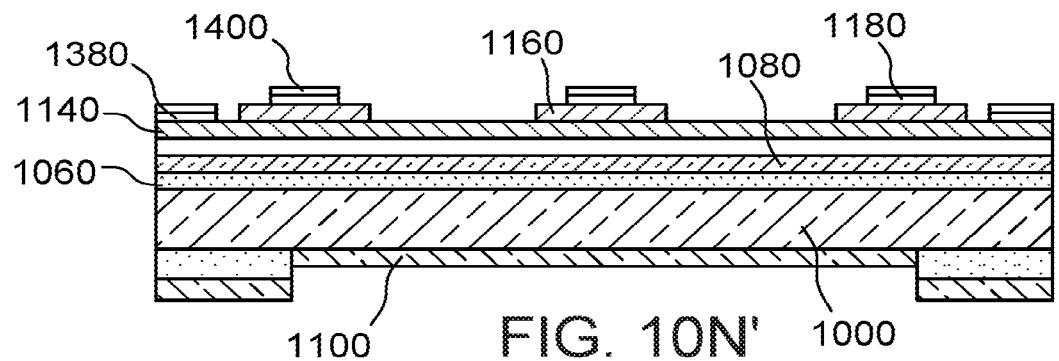
Figure 10O:
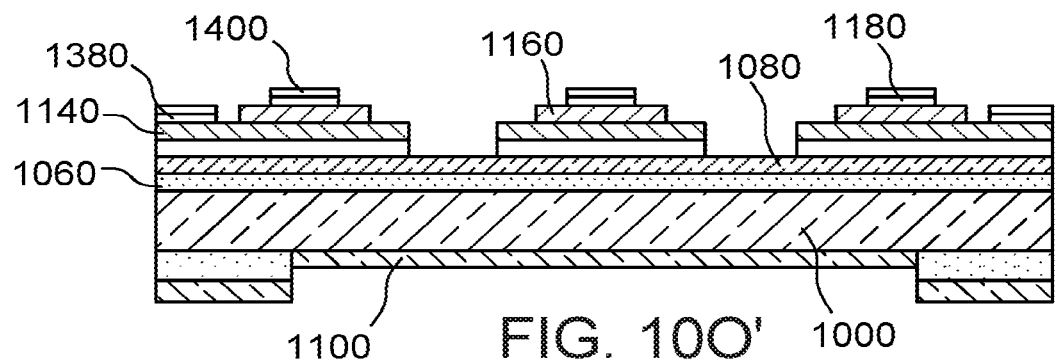
Figure 10P:
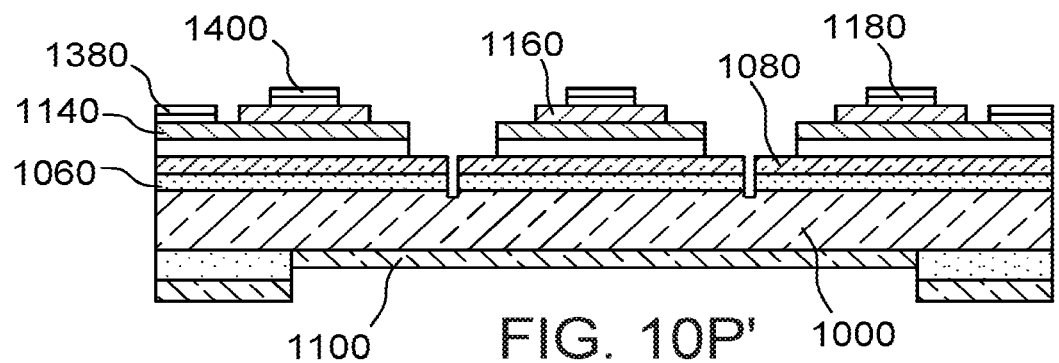
Figure 10Q:
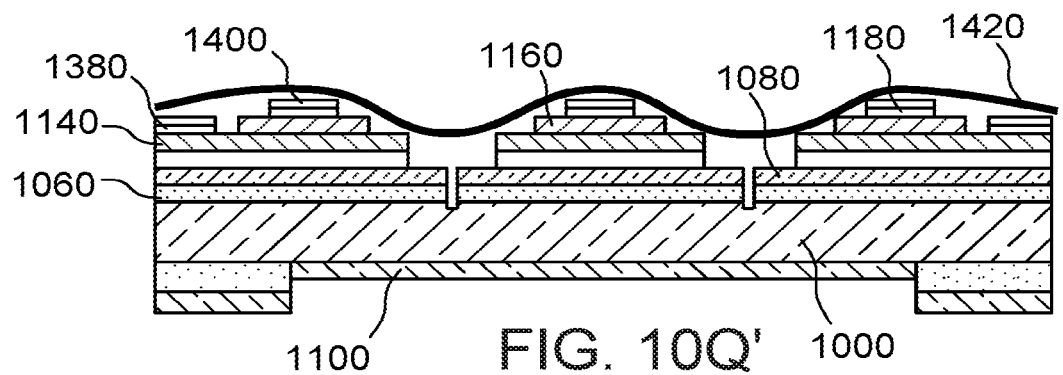
Figure 10R:
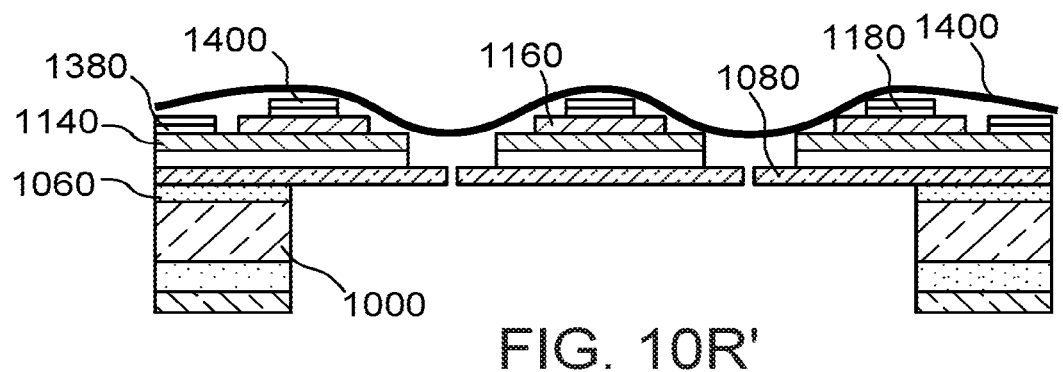

The steps are represented schematically in FIGS. 10A to 10S.

For example, a silicon substrate 1000 represented in FIG. 10A is used, having for example a thickness of 725 μm and a diameter of 200 mm. A glass substrate for example may be envisaged.

During a first step, a thermal oxidation of the substrate is carried out so as to form an oxide layer 1020 on all the surfaces of the substrate, of a thickness of 2 μm for example. The element thereby obtained is represented in FIG. 10B.

Then, a hard mask of oxide 1040 is produced on the rear face of the substrate. This mask has for example a thickness of 7 μm. The mask is produced by turning over the substrate; as a function of the chosen deposition composition, it is possible to deposit the mask only on this face. It may be for example a PVD (Physical Vapour Deposition) type deposition. The element thereby obtained is represented in FIG. 10C.

A lithography is then carried out on the hard mask. The element thereby obtained is represented in FIG. 10D.

During a following step, the hard mask and the oxide layer 1020 on the rear face are etched, for example by reactive ion etching, so as to reach the rear face of the substrate 1000. The element thereby obtained is represented in FIG. 10E.

During a following step, the oxide layer on the front face is removed, for example by de-oxidation or chemical etching. The element thereby obtained is represented in FIG. 10F.

During a following step, an oxide layer 1060 is formed on the front face. Advantageously, a densification annealing takes place for example at a temperature of the order of 800° C. The element thereby obtained is represented in FIG. 10G.

During a following step, a layer 1080 is formed on the front face intended to form the membrane 2, and a layer 1100 on the rear face. Preferably, these layers are for example made of polysilicon, SiC or SiO$_2$. The thickness of the layers 1080, 1100 is for example comprised between several hundreds of nm to several μm, or even several tens of μm.

The layers 1080, 1100 are for example produced by CVD (Chemical Vapour Deposition) or by epitaxial growth. Preferably, the stresses of the layers 1080, 1100 are controlled.

The layers 1080, 1100 may be formed in several steps. For example, for a thickness of 4 μm, two layers of 1.5 μm thickness and one layer of 1 μm thickness are produced successively.

Advantageously an annealing step then takes place. The element thereby obtained is represented in FIG. 10H.

During a following step, a layer 1120 is formed on the layer 1080 for example made of SiO$_2$ or SiN, having for example a thickness comprised between several hundreds of nm and several μm. The layer 1120 is formed for example by thermal oxidation or by CVD. Advantageously, a densification annealing takes place for example at a temperature of the order of 800° C.

The element thereby obtained is represented in FIG. 10I.

During a following step, the first and second actuators are produced.

To do so, firstly a layer 1140 is produced intended to form the lower electrodes of the actuators, for example made of Pt or Mo. The layer 1140 is produced for example by deposition on the layer 1120. The layer 1140 has for example a thickness comprised between several tens of nm to several hundreds of nm. The element thereby obtained is represented in FIG. 10J.

A layer of piezoelectric or ferroelectric material 1160 is then formed on the layer 1140, for example made of PZT, AlN, ZnO, LNO of which the thickness is for example comprised between several hundreds of nm to several μm.

The upper electrode is then produced by formation of a layer 1180 on the piezoelectric or ferroelectric material 1160, for example made of Ru or Au for example of thickness comprised between several tens of nm to several hundreds of nm. The element thereby obtained is represented in FIG. 10K.

Then etching steps take place.

Firstly, the layer 1180 is etched so as to delimit the annular actuator 16 and the disc-shaped actuator 14.

Then, the layer 1160 made of piezoelectric or ferroelectric material is etched.

The element thereby obtained is represented in FIG. 10L.

Then, the remaining portions of layer 1180 are once again etched so that they are set back with respect to the portions of layer 1160. The element thereby obtained is represented in FIG. 10M.

The layer 1140 is then etched, as well as the oxide layer 1120.

Preferably, a stepped profile is produced. This is obtained because all the layers are deposited then etched, from the upper layer, using different photolithography masks, the second mask being wider than the first, etc. This makes it possible to leave safety margins to avoid covering layers, which could arise due to the uncertainty of positioning of the masks. In this way any electrical short-circuit between the electrodes is avoided. The element thereby obtained is represented in FIG. 10N.

During the following steps, the pads 1200 for electrical contact are produced. Beforehand, a layer 1220 of dielectric material is formed, for example made of SiO$_2$ on the edges of the stacks formed of the lower, upper electrodes and the piezoelectric material, this layer being etched so as to clear partially the lower and upper electrodes. The element thereby obtained is represented in FIG. 10O.

Then, a layer for example made of AlSi or TiAu is formed and is etched, thereby forming contact pads at the level of the areas where the electrodes have been cleared. The element thereby obtained is represented in FIG. 10P.

Advantageously, during a following step a protective layer 1240 is formed on the actuators, for example an oxide layer, in order to protect the actuators from contact with the stop elements. The thickness of this layer may be comprised between several hundreds of nm to several μm, for example 500 nm.

During a following step the layer 1240 is etched, to access to the electrical contacts.

The element thereby obtained is represented in FIG. 10Q.

Preferably, during a following step, the actuators are protected, for example by the deposition of a dry film 1260. Then, the rear face is etched in order to release the membrane 2.

The membrane is released by deep etching of the substrate via the rear face until reaching the membrane.

The element thereby obtained is represented in FIG. 10R.

In order to be able to be used in liquid medium, a suitable packaging is produced. The cavity formed on the side of the rear face of the membrane is closed by a cover 1280. In fact the rear face of the membrane is preferentially used to carry out the sorting of cells, which simplifies the electrical connections of the actuators situated on the front face. Nevertheless since the actuators are encapsulated, the front face provided with actuators may also serve for sorting by adapting the electrical connections. By using both the rear face and the front face, the sorting capacity of the device is doubled. The two faces of the membrane may have the same adhesion properties with respect to different types of cells or different properties, to do so one of the faces may be functionalised.

The cover 1280 is for example made of glass and is for example bonded onto the layer 1100. It is provided that the cover comprises an inlet orifice 1300 and an outlet orifice 1320 for the liquid containing the cells.

Moreover, the device is arranged on supports 1340 so as to suspend the membrane and to enable it to be made to vibrate. The supports may be mechanical supports or a part of an electronic circuit board. In an advantageous manner, the supports are also used for the electrical supply by means of microelectrical connections 1360. The microelectrical connections are obtained for example by stretching microwires, for example made of gold, which are welded onto the contact pad on one side, and onto the electronic card on the other side.

The element thereby obtained is represented in FIG. 10S. The cells are symbolised by stars.

The device may form part of a microdevice, for example it may form a part of the surface of a microfluidic chamber in the case of a sorting device. It may form part of a microfluidic circuit and assure the protection of the inside of certain channels.

In the example represented in FIG. 10S, the vibrating support forms the bottom of the chamber but this is in no way limiting and it may form a lateral wall or even an upper wall. It will then be verified that these walls effectively come into contact with the solution comprising the cells.

To produce a device according to FIGS. 5A to 9B, the steps of production represented in FIGS. 10A to 10Q are similar. At the step represented in FIG. 10R, a film made of flexible material, for example made of polymer material, is deposited instead of the dry film. Then the treatment support is released by deep etching of the substrate via the rear face until the treatment support is reached.

The devices represented in FIGS. 5A to 7B may be produced according to the following method.

The steps 10A to 10M are similar.

A layer 1380 for example of ruthenium and then a layer 1400 for example of gold are formed. An etching is then carried out so as to define ruthenium-gold contact pads on the material PZT and on the edge of the layer 1140.

The element thereby obtained is represented in FIG. 10N'.

The layer 1140 is then etched, as well as the oxide layer 1120.

Preferably, a stepped profile is produced. This is obtained because all the layers are deposited then etched, from the upper layer, using different photolithography masks, the second mask being wider than the first, etc. This makes it possible to leave safety margins to avoid covering layers, which could arise due to the uncertainty of positioning of the masks. Any electrical short-circuit between the electrodes is thus avoided. The element thereby obtained is represented in FIG. 10O'.

During a following step, the layers 1080, 1060 and over a part of its thickness the layer 1000 are etched in order to define beams. The element thereby obtained is represented in FIG. 10P'.

During a following step, a dry film 1420 is deposited on the front face of the element of FIG. 10P'. The dry film serves to protect the front face of the element during the deep etching that is going to follow. The film is then advantageously conserved to form the flexible support on which the cells are going to adhere. This support will be deformed by activation of the actuators.

The element thereby obtained is represented in FIG. 10Q'.

During a following step, the rear face is etched in order to release the beams by deep etching. The substrate 1000 and the oxide layer 1060 are etched until the beams are reached.

The element thereby obtained is represented in FIG. 10R'.

The invention claimed is:

1. Device for treating at least one biological cell comprising:
    at least one treatment support comprising a receiving surface enabling the adhesion of said at least one biological cell,
    at least one actuator configured to deform said treatment support in order to apply a stress to said at least one biological cell, and
    a control circuitry configured to control said at least one actuator such that the actuator deforms the treatment support according to a given amplitude of deformation and for a given treatment duration so as to apply said stress to the cell for said treatment duration, wherein
    said amplitude of deformation is such that it generates at least one transitory pore in a membrane of the biological cell so as to treat said cell, and
    said at least one actuator is configured to apply an energy to said at least one biological cell of about $1 \times 10^{-18}$ J.

2. Treatment device according to claim 1, in which said given amplitude of deformation makes it possible to determine the mechanical response of the cell to the stress so as to characterise it.

3. Treatment device according to claim 1, in which said treatment support is contained mainly in the median plane and in which said actuator is configured to deform the treatment support along an out-of-plane direction.

4. Treatment device according to claim 1, in which said treatment support is contained mainly in the median plane and in which said actuator is configured to deform the treatment support mainly in said median plane.

5. Treatment device according to claim 1, comprising a plurality of actuators arranged so as to together apply an axisymmetric deformation to the treatment support to deform one biological cell.

6. Treatment device according to claim 1, comprising one actuator or several actuators arranged so as to produce a deformation about a median plane perpendicular to a plane of the treatment support.

7. Treatment device according to claim 1, in which all or part of the surface of the treatment support is functionalised so as to modify the adhesion force of the type or types of biological cells to treat with respect to the non-functionalised surface.

8. Treatment device according to claim 1, in which said actuator is a piezoelectric or ferroelectric or thermal actuator.

9. Treatment device according to claim 1, in which said actuator is an electrostatic or magnetic actuator.

10. Treatment device according to claim 1 in which said treatment support is contained mainly in the median plane and in which said actuator is configured to deform the treatment support mainly in said median plane, in which said treatment support is made of flexible material and in which said at least one actuator is such that it can apply a tensile force to an edge area of the treatment support in said median plane.

11. Treatment device according to claim 10 in which the at least one actuator is an electrostatic actuator comprising a moveable comb and a fixed comb defining between them an air gap, the treatment support being suspended between the two combs, the variation of said air gap applying a tensile stress to said treatment support.

12. Treatment device according to claim 1, in which the treatment support is made of a flexible material and in which the at least one actuator comprises at least one fixed-free beam and a piezoelectric or ferroelectric material secured to the beam, such that the deformation of the piezoelectric or ferroelectric material causes an out-of-plane deformation of the beam and the treatment support.

13. Treatment device according to claim 12, comprising several actuators spread out at the level of an outer edge of the treatment support.

14. Treatment device according to claim 1, being a MEMS and/or NEMS device.

15. Treatment device according to claim 10, comprising at least two actuators applying a tensile force in opposite directions to two opposite edges of the treatment support.

16. Treatment device according to claim 10, in which the at least one actuator is an electrostatic actuator comprising a moveable comb and a fixed comb defining between them an air gap, the treatment support being suspended between the two combs, the reduction, of said air gap applying a tensile stress to said treatment support.

17. Treatment device according to claim 1, wherein
the control circuitry controls said at least one actuator such that the actuator deforms the treatment support in a plane of the support to produce an out of plane deformation to the membrane generating the at least one transitory pore.

18. Treatment device according to claim 1, wherein
the control circuitry controls said at least one actuator such that the actuator deforms the treatment support in a plane of the support to produce tangential stress in a plane of the membrane generating the at least one transitory pore.

19. Treatment device according to claim 1, wherein
the treatment support has a disc shape and actuators arranged radially on the disc; and
the control circuitry controls said actuators to deform the actuators and the treatment support in an approximate truncated cone shape to deform the membrane and generate the at least one transitory pore.

20. Treatment device according to claim 1, wherein
the control circuitry controls said actuators to deform the treatment support to apply tensile stress to deform the membrane and generate the at least one transitory pore.

21. Treatment device according to claim 1, comprising:
a casing disposed around the receiving surface;
a fluid supply inlet disposed in the casing; and
a fluid supply outlet disclosed in the casing.

22. Treatment device according to claim 21, comprising:
the inlet and outlet being arranged such that fluid flowing from said inlet to said outlet flows over the receiving surface.

23. Treatment device according to claim 1, wherein the actuator deforms the treatment support according to the given amplitude of deformation for a duration on the order of several seconds so as to apply said stress to one of a human macrophage and a human dendritic cell.

24. Microfluidic cellular delivery device comprising at least one treatment device according to claim 1, a fluidic circuit for supplying a solution comprising at least one biological cell to treat, an evacuation circuit for evacuating the fluid and a supply circuit for supplying a solution comprising the elements to introduce into said at least one cell.

* * * * *